(12) United States Patent
Ebstein

(10) Patent No.: US 10,346,964 B2
(45) Date of Patent: Jul. 9, 2019

(54) SYSTEM FOR ACTINIC INSPECTION OF SEMICONDUCTOR MASKS

(71) Applicant: Steven M. Ebstein, Newton, MA (US)

(72) Inventor: Steven M. Ebstein, Newton, MA (US)

( * ) Notice: Subject to any disclaimer, the term of this patent is extended or adjusted under 35 U.S.C. 154(b) by 144 days.

(21) Appl. No.: 15/423,239

(22) Filed: Feb. 2, 2017

(65) Prior Publication Data

US 2017/0221194 A1    Aug. 3, 2017

Related U.S. Application Data

(60) Provisional application No. 62/290,139, filed on Feb. 2, 2016.

(51) Int. Cl.
| | |
|---|---|
| *G06T 7/00* | (2017.01) |
| *H01S 3/09* | (2006.01) |
| *G02B 5/18* | (2006.01) |
| *G01N 21/956* | (2006.01) |
| *G02B 21/00* | (2006.01) |

(52) U.S. Cl.
CPC ......... *G06T 7/0004* (2013.01); *G01N 21/956* (2013.01); *G02B 5/1876* (2013.01); *G02B 21/0056* (2013.01); *H01S 3/0903* (2013.01); *G01N 2021/95676* (2013.01); *G06T 2207/30148* (2013.01)

(58) Field of Classification Search
CPC .. G06T 7/0004; G02B 5/1876; G02B 21/0056
See application file for complete search history.

(56) References Cited

U.S. PATENT DOCUMENTS

| | | | | | |
|---|---|---|---|---|---|
| 5,539,514 | A | * | 7/1996 | Shishido | G01N 21/94 356/237.4 |
| 9,574,868 | B2 | * | 2/2017 | Shaked | G01B 9/02057 |
| 9,632,039 | B2 | * | 4/2017 | Den Boef | G01B 11/00 |
| 2016/0187849 | A1 | * | 6/2016 | Zhang | G02B 21/0016 348/41 |
| 2016/0266057 | A1 | * | 9/2016 | Dudovich | G03H 1/0866 |

OTHER PUBLICATIONS

Ackermann, W. et al., "Operation of a free-electron laser from the extreme ultraviolet to the water window", Nature Photonics 1, 2007, pp. 336-342.

(Continued)

*Primary Examiner* — Jonathan R Messmore
(74) *Attorney, Agent, or Firm* — Pandiscio & Pandiscio

(57) ABSTRACT

An apparatus and method are disclosed for actinic inspection of semiconductor masks intended for extended ultraviolet (EUV) lithography, or similar objects, with feature sizes less than 100 nm. The approach uses a coherent light source with wavelength less than 120 nm. Inside a vacuum system, an optical system directs the light to an object, i.e., the mask or mask blank, and directs the resulting reflected or transmitted light to an imaging sensor. A computational system processes the imaging sensor data to generate phase and amplitude images of the object. The preferred imaging modality, a form of digital holography, produces images of buried structures and phase objects, as well as amplitude or reflectance images, with nanometer resolution less than or equal to the feature size of the mask.

14 Claims, 5 Drawing Sheets

Schematic of the optics with a reflective object representing the EUV mask. This shows generation of an expanding beam using an off-axis Fresnel zone plate lens. The IR ultrafast laser co-propagating with the HHG x-ray beam is filtered by thin metal films. Any remaining IR will be rejected by pinhole stops or by reflection at a different angle. The compound zone plate generates an off-axis reference beam that resolves ambiguities for the reconstruction. Some distances are not to scale to highlight functionality. The continuation of the IR beam admixture (orange/red) past the zone plate is not shown for clarity.

(56) References Cited

OTHER PUBLICATIONS

Allaria, E. et al., "Highly coherent and stable pulses from the FERMI seeded free-electron laser in the extreme ultraviolet", Nature Photonics, vol. 6, No. 10, 2012, pp. 699-704.
Benk, Markus P. et al., "Demonstrations of 22-nm half inch resolution on the SHARP EUV microscope", Journal of Vacuum Science and Technology, vol. 6, 2015.
Garcia-Sucerquia, Jorge et al., "Digital in-line holographic microscopy", Appl. Opt., vol. 45, 2006, pp. 836-850.
Garretto et al., "Aerial imaging technology for photomask qualification: from a microscope to a metrology tool" Advanced Optial Technologies, vol. 2 No. 4, 2012, pp. 289-298.
Goldberg et al., "Commissioning an EUV mask microscope for lithography generations reaching 8 nm", Proc. SPIE 8679, 2013.
Goldberg, K.A. et al., "Wavelength-Specific Reflections: A Decade of EUV Actinic Mask Inspection Research", J. Vac. Sci. Technol., vol. 6, 2010.
Guizar-Sicarios, Manuel et al., "Direct image reconstruction from a Fourier intensity pattern using HERALDO", Opt. Lett. vol. 33, 2008, pp. 2668-2670.
Krenkel, M. et al., "Transport of intensity phase reconstruction to solve the twin image problem in holographic x-ray imaging", Opt. Express, vol. 21, 2013, pp. 2220-2235.
Latychevskaia, Tatiana et al., "Solution to the Twin Image Problem in Holography", Phys. Rev. Lett., vol. 98, 2007.
Makowski, M. et al., "Three-plane phase-only computer hologram generated with iterative Fresnel algoritm", Opt. Eng., vol. 44, No. 12, 2005.
Paul, Ariel J., "Coherent EUV Light from High-Order Harmonic Generation: Enhancement and Applications to Lensless Diffractive Imaging", PhD. dissertation, University of Colorado, 2007.
Seaberg, M. et al., "Ultrahigh 22 nm resolution coherent diffractive imaging using a desktop 13 nm harmonic source", Opt. Exp., vol. 19, 2011.
Talanov, V.I., "Focusing of light in cubic media", Sov. Phys. JETP Lett., vol. 11, 1970, pp. 199-201.
Wack, D. et al., "Solutions for EUV Mask and Blank Inspections" KLA Tencor, 2012.
Wang et al., "Recording conditions of digital holography", Proc. SPIE 6279, 27th International Congress on High-Speed Photograph and Photonics, 62791J (Jan. 11, 2007), doi: 10.1117/12.725187.
Fleck, Jr. et aL, "Time-Dependent Propagation of High Energy Laser Beams through the Atmosphere", Appl. Phys. vol. 10, 1976, pp. 129-160.
Leith, Emmett N. et al., "Wavefront Reconstruction with Continuous-Tone Objects", J. Opt. Soc. Am., vol. 53, 1963, pp. 1377-1381.

* cited by examiner

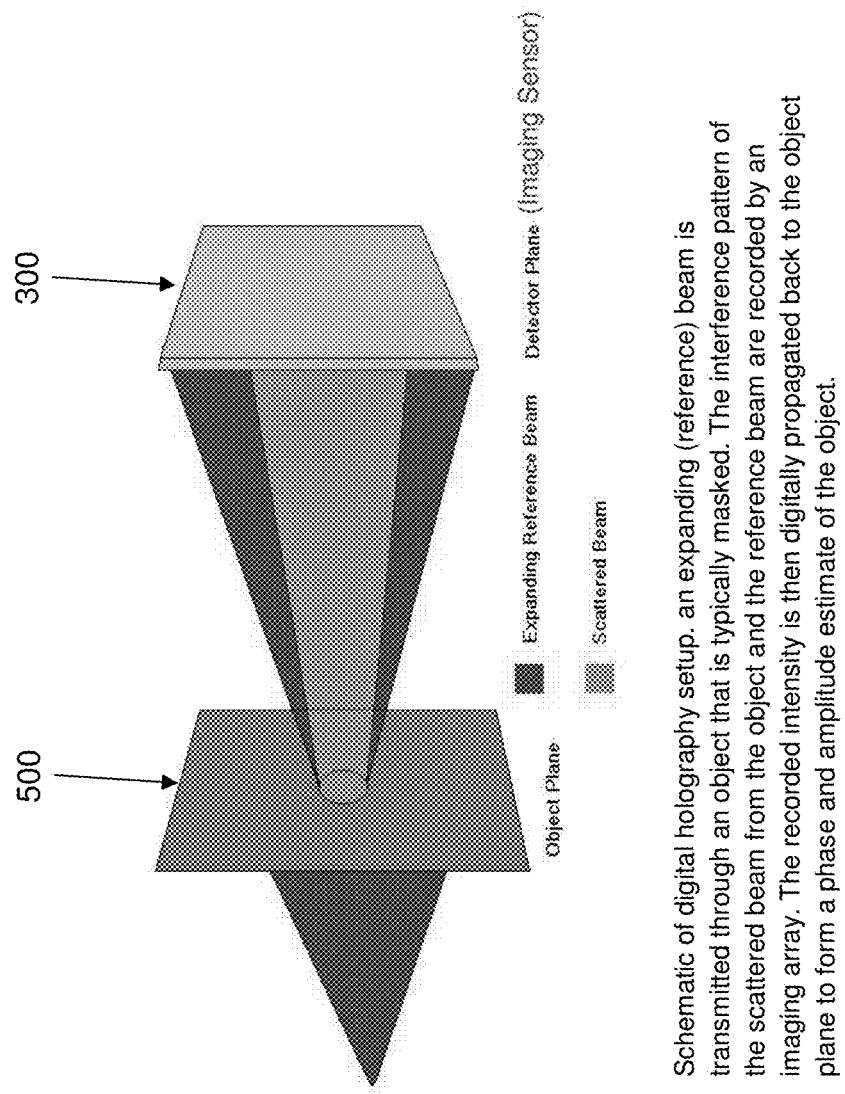

FIG. 2

Schematic of digital holography setup. an expanding (reference) beam is transmitted through an object that is typically masked. The interference pattern of the scattered beam from the object and the reference beam are recorded by an imaging array. The recorded intensity is then digitally propagated back to the object plane to form a phase and amplitude estimate of the object.

Schematic diagram of an off-axis Fresnel zone plate lens (a) and a portion of a freestanding gold film zoneplate used in the SHARP instrument (b). In this design, the clear zones of the plate are stenciled so the film can maintain mechanical rigidity.

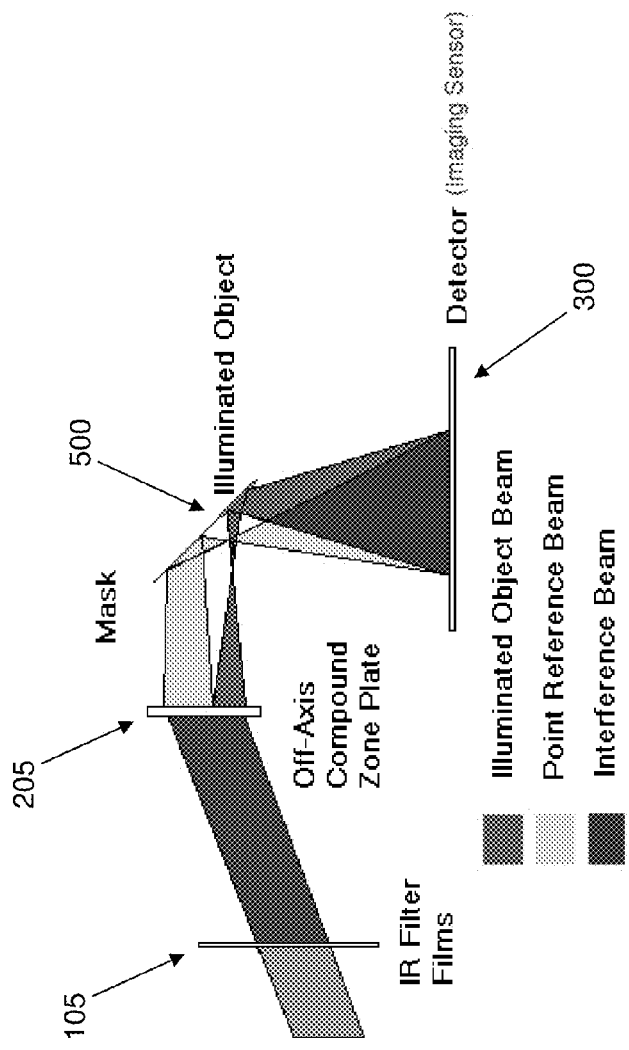

FIG. 4

Schematic of the optics with a reflective object representing the EUV mask. This shows generation of an expanding beam using an off-axis Fresnel zone plate lens. The IR ultrafast laser co-propagating with the HHG x-ray beam is filtered by thin metal films. Any remaining IR will be rejected by pinhole stops or by reflection at a different angle. The compound zone plate generates an off-axis reference beam that resolves ambiguities for the reconstruction. Some distances are not to scale to highlight functionality. The continuation of the IR beam admixture (orange/red) past the zone plate is not shown for clarity.

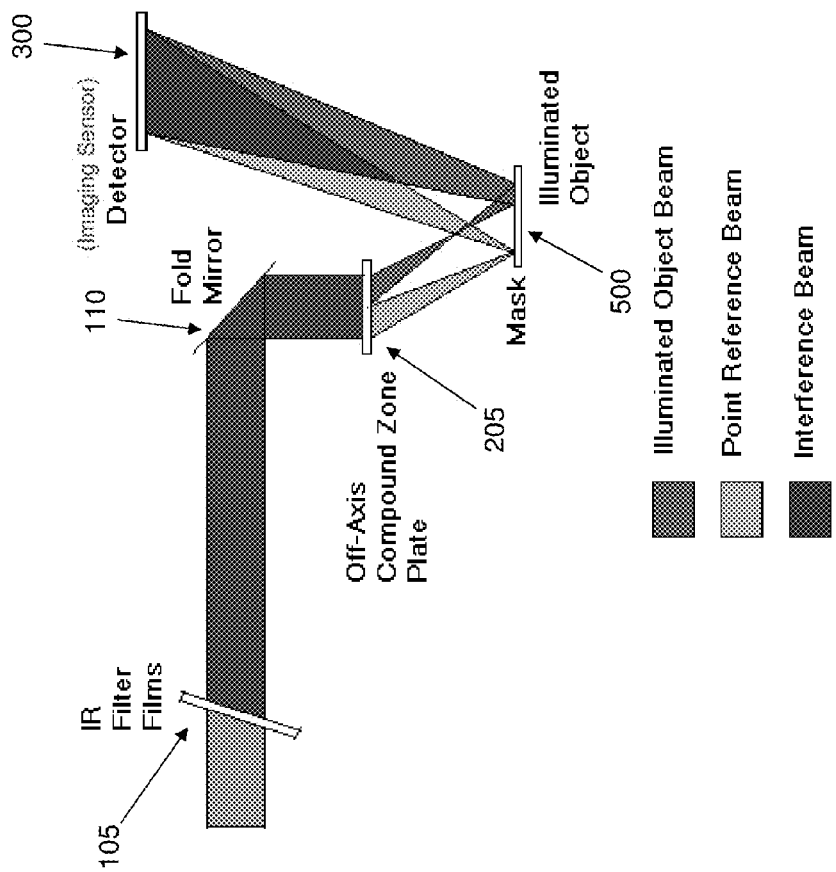

Schematic of the optics setup for scanning a reflective EUV mask. After IR filtering, the beam is folded down towards the compound off-axis Fresnel zone plate. One portion of the beam creates a point source near the mask surface and a second portion illuminates the region of interest. The two beams interfere at the detector to form the hologram. Some distances and angles are not to scale.

FIG. 5

SYSTEM FOR ACTINIC INSPECTION OF SEMICONDUCTOR MASKS

REFERENCE TO PENDING PRIOR PATENT APPLICATION

This patent application claims benefit of pending prior U.S. Provisional Patent Application Ser. No. 62/290,139, filed Feb. 2, 2016 by Steven M. Ebstein for SYSTEM FOR ACTINIC INSPECTION OF SEMICONDUCTOR MASKS, which patent application is hereby incorporated herein by reference.

FEDERALLY SPONSORED RESEARCH

None

FIELD OF THE INVENTION

The present invention pertains to a system for actinic inspection of semiconductor masks that images buried structures and phase objects as well as amplitude (or reflectance). The present invention relates to digital holographic microscopy with nanometer resolution.

BACKGROUND OF THE INVENTION

Semiconductor manufacturers strive to reduce the size of devices in order to reduce power consumption and increase gate density and thereby deliver faster circuits with greater processing power at lower cost to their customers. This has led to development of generations of photolithographic equipment for patterning the semiconductor wafers where the minimum feature size, e.g., the width of the smallest patterned line, has shrunk with each successive generation. Most high-resolution equipment currently in use can produce 14 nm feature sizes with the industry planning to move to smaller feature sizes in the near future.

Current practice typically uses UV light at 193 nm wavelength when patterning the semiconductor wafer. In order to produce features significantly smaller than the wavelength, immersion lithography is used to reduce the wavelength below by forming the image in a liquid with refractive index >1, as well as using multiple patterning to produce features smaller than the spot width. It is generally accepted that moving to smaller features will require extreme ultraviolet (EUV) lithography. While EUV typically refers to wavelengths between 120 nm and 10 nm, it is generally expected that this next-generation lithography will use 13.5 nm light emitted by laser-produced plasma sources with $CO_2$ lasers exciting tin droplets. Future generations may require soft x-ray (SXR) lithography with wavelengths <10 nm.

In order to efficiently and economically produce good parts, the masks used in the photolithographic process must be nearly free of defects. This typically requires inspection of the masks at multiple points in the masks life cycle. The blanks must be inspected before and after the mask pattern is produced, when a potential defect has been identified in a mask in use for lithography, and/or after a defect has been repaired.

The masks used for semiconductor photolithography are oversized with the mask image demagnified at the surface of the wafer, typically by 4x. Thus, a 22 nm feature is 88 nm at the mask and a 14 nm feature is 56 nm at the mask. This dimension is smaller than the Abbe resolution limit, related to the inspection wavelength, of currently developed optical inspection tools that generally use wavelengths of 193 nm and longer.

A variety of approaches have been developed to inspect the masks and mask blanks. Typically, these approaches must image the mask with a resolution comparable to or smaller than the feature size of the process in order to reliably spot significant defects in the mask. The challenge is to do so with an affordable instrument which can reliably identify and analyze defects significant enough to affect the lithography process.

One approach for inspecting the masks or mask blanks uses synchrotron radiation as the illuminating light source. Using relatively bright synchrotron light (see K. A. Goldberg, I. Mochi, "Wavelength-Specific Reflections: A Decade of EUV Actinic Mask Inspection Research," *J. Vac. Sci. Technol. B* 28 (6), C6E1-10 (2010). DOI 10.1116/1.3498757), which has an arbitrarily selectable wavelength, EUV microscopes can image significant areas of EUV masks with resolution down to 22 nm, with current technology (see Markus P. Benk, Kenneth A. Goldberg, Antoine Wojdyla, Christopher N. Anderson, Farhad Salmassi, Patrick P. Naulleau, and Michael Kocsis, "Demonstration of 22-nm half pitch resolution on the SHARP EUV microscope," *Journal of Vacuum Science and Technology B*33 (6), 06FE01 (2015). DOI 10.1116/1.4929509). However, synchrotrons are large accelerators that are quite expensive and require large, dedicated facilities, which imposes significant practical limitations, i.e., cost and availability, on their utility for mask inspection. In addition, these synchrotron inspection systems have not yet achieved finer resolution for routine imaging, so there is room for improvement using different imaging techniques.

It is far more desirable to perform EUV mask inspection with a smaller instrument that can be installed in a semiconductor fabrication facility. Such an instrument would have lower cost and much higher availability than large, dedicated synchrotron facilities and would integrate into the workflow of the fabrication facility. KLA-Tencor described a concept for an EUV mask inspection platform labeled the 710 System (see "Solutions for EUV Mask and Blank Inspections 2012 D. Wackand G. Inderhees.pdf"). This proposed system (designated the 7xx tool) has a module located inside the cleanroom with dimensions 9 m×3 m×3.1 m (length×width×height) and 2 modules in the room below, outside the cleanroom, each with comparable footprints and volumes as the module inside the cleanroom. Such a system is small enough to be installed as one of the suite of instruments present in the cleanroom of a semiconductor fabrication facility and hence be used in the normal workflow.

Currently proposed systems for EUV mask inspection typically use one of three approaches to inspect masks with the highest resolution: (1) inspection is done optically with UV light of 193 nm or longer, which has a short enough wavelength to detect many features but can still transmit through air and some optical materials like fused silica; (2) inspection is done with scanning electron or ion beams, as in a scanning electron microscope (SEM); and (3) inspection is done with a scanning tunneling microscope, such as an atomic force microscope (AFM).

Each of these approaches has some practical drawbacks. Approach (1) is limited in resolution by the wavelength of the light used. Approaches (2) and (3) are limited by the scanning rate of the microscope and hence the throughput they can achieve. Approach (2) is also limited logistically by the vacuum environment it requires. Approach (3) is also limited in that the tip of the scanning tunneling microscope cannot penetrate the surface of the object, unlike approaches that use radiation which may penetrate to some depth and hence can provide some information about the material underlying the surface or its three dimensional composition.

However, the greatest drawback to these approaches is they do not directly measure the characteristic that can predict the pattern the mask will project when used for lithography, namely, spatially varying reflectivity of the mask at the relevant wavelength. Approach (1) senses the reflectivity at a different wavelength. Approaches (2) and (3) do not image the reflectivity of electromagnetic radiation; instead, they measure interaction with a charged particle or tunneling to a very sharp tip.

Industry experts generally agree that EUV lithography will require actinic inspection, i.e., inspection done with the same wavelength as when performing the photolithography. This expectation stems from two facts: (1) the resolution of an optical system scales with the operating wavelength as $R=k\lambda/NA$, where k is a process factor, $\lambda$ is the wavelength, and NA is the numerical aperture of the objective lens, so a shorter wavelength can resolve smaller features; and (2) the effect of a defect is best gauged by its effect on light of a wavelength comparable to what will be used during the photolithography process.

The second point is especially important since some mask defects are primarily phase defects, i.e., they change the phase of the light projected onto the wafer. For EUV lithography, the mask, like all of the optics, is reflective, since transmission losses are too large for practical materials. The mask is formed by applying a patterned reflective coating to a substrate. At EUV wavelengths, reflective coatings are Bragg reflectors, a stack of thin film coatings designed for high reflectivity, produced in a manner similar to multilayer dielectric coatings for visible and near-visible wavelengths. The coatings are typically multilayer stacks of silicon and molybdenum with tens of layers.

If there is a defect or particle on the substrate, it is possible that the multilayer coating will be reflective, but will have a phase shift due to the local surface being higher or lower than the surrounding surface. A similar effect can occur with a particle or defect that is embedded in the multilayer coating. Due to the stringent resolution requirements and partial coherence of the EUV illumination used during lithography, these phase shift errors can significantly affect the geometry or the sharpness of the geometry patterned by the lithography. However, these phase shift errors may not be detectable using non-actinic radiation for inspection, e.g., longer wavelength light (193 nm) or the electron beam of a scanning electron microscope (SEM). More generally, a possible defect may affect a non-actinic radiation beam much differently than the actinic beam. Hence inspection with actinic radiation is preferred to inspection with non-actinic radiation, in order to better predict the defect's affect on the photolithography, along with the ability to detect phase defects.

One approach to this problem would be to use conventional EUV sources, similar to those in development or in use for EUV lithography, together with conventional optical systems similar to those used with 193 nm inspection tools, except for their use of reflective optics. These conventional EUV sources create a hot plasma which then radiates at ~13.5 nm, either by using powerful $CO_2$ lasers to turn tin droplets into plasma or by some other means of creating and exciting the plasma. For EUV wavelengths, the optical system consists of reflective optics whose surface figures (a term of art referring to the accuracy with which an optical surface conforms to its intended shape) are accurate enough for 13.5 nm light, over an order of magnitude more accurate than optics for 193 nm tools.

Such a system has many drawbacks. The optical system is expensive due to its complexity and exacting specifications. The plasma sources typically produce ions which erode the optical surfaces over time. The optical system performs incoherent imaging which is not very sensitive to phase defects. And the very short wavelengths require that the focal distance, i.e. the distance from the mask surface to the optics, be controlled with extremely tight tolerances, which can be very challenging when scanning across a mask that is ~10 cm across.

Such systems have been produced, for example the EUV AIMS system produced by Zeiss (see Garetto et al., Advanced Optical Technologies. Volume 1, Issue 4, Pages 289-298, ISSN (Online) 2192-8584, ISSN (Print) 2192-8576, DOI: https://doi.org/10.1515/aot-2012-0124, September 2012). However, due to the drawbacks mentioned, these systems are not capable of scanning an entire mask for comprehensive inspection. Instead, they are used exclusively for limited imaging of small regions of a mask, often for a task titled "defect review" where a defect has already been identified, perhaps because a test lithography run yielded a device which did not perform properly when tested electrically.

There exists a need for an actinic mask inspection system for EUV lithography that can examine masks for defects using a comparable wavelength to the one that will be used for photolithography. The system should be able to image phase defects as well as amplitude defects, and scan masks with adequate throughput to inspect the entire mask in a reasonable period of time. The system should also be significantly less complicated than an approach that requires mirrors whose surface figures and alignment must be accurate to several nanometers while scanning across the surface of the mask.

One approach others have taken is a coherent imaging approach capable of imaging phase and amplitude defects. Termed coherent diffractive imaging (CDI), the object is illuminated with a coherent beam. An imaging sensor records an image of the intensity of the diffraction pattern (see M. Seaberg, et al., "Ultrahigh 22 nm resolution coherent diffractive imaging using a desktop 13 nm harmonic source," Opt. Exp. 19, 22470 (2011)). Since much of the light is transmitted or reflected in the 0th order, it must be blocked with a beam stop along the optical axis so as not to wash out the off-axis diffraction pattern. This method uses iterative phase retrieval algorithms, typically with some finite support constraints, to estimate the phase and amplitude object from the diffraction intensity.

While CDI does yield relatively high resolution images, it is an inefficient use of the beam energy, since much of the beam is lost in the 0th order. It also requires many iterations, hence lengthy computations, to produce the output. The number of iterations required to obtain a high quality reconstruction is not predictable and may take tens or hundreds of iterations. This computation, along with the inefficient use of the illuminating beam, represent serious limitations to using CDI for inspection tasks. It would be much more advantageous to use an approach that produces deterministic imagery which can be produced in real time.

In the following specification, we shall use conventional optical imaging nomenclature to refer to the target of the system as the object. Our discussion centers on application to the inspection and imaging of reflective EUV semiconductor lithography masks. However, it will be appreciated that with modifications obvious to those skilled in the art, the present invention has general application to imaging other objects with comparable resolution, including objects imaged in transmission.

SUMMARY OF THE INVENTION

In accordance with preferred embodiments of the present invention, an apparatus and method are provided for performing actinic inspection of semiconductor masks with feature sizes of less than 100 nm. The apparatus provides a coherent source of light with a wavelength of less than 120 nm. Inside a vacuum system, an optical system directs the light to an object, i.e., the mask or mask blank, and directs the resulting reflected or transmitted light to an imaging sensor such as a CCD or CMOS array. A computational system processes the image sensor data to generate phase and amplitude images of the object.

In a preferred form of the present invention, the source comprises a gas cell which generates the coherent light characterized generally by a propagation direction using high harmonic generation (HHG) from an intense pulse of an ultrafast laser.

In a preferred form of the present invention, the source comprises a compact free electron laser (FEL) which generates the coherent light characterized generally by a propagation direction by passing an electron beam through a periodic arrangement of magnets with alternating poles across the beam path known as an undulator.

In a preferred form of the present invention, the optical system includes a focusing optic that concentrates the illumination beam onto the object.

In a preferred form of the present invention, the optical system comprises an off-axis Fresnel zone plate (FZP) which illuminates the object.

In a preferred form of the present invention, the optical system effectively forms two or more beams. At least one beam illuminates the object and interferes with at least one other beam in the image sensor plane. The two interfering beams are effectively offset laterally relative to the propagation direction in order to resolve the twin ambiguity when reconstructing the object.

In a preferred form of the present invention, a back-illuminated CMOS array serves as the imaging sensor.

In a preferred form of the invention, the computational system uses special purpose computational hardware to rapidly reconstruct the object in real-time.

In a preferred form of the invention, there is provided an apparatus for imaging an object with resolution less than 100 nm, the apparatus comprising:
  a coherent light source with wavelength less than 120 nm;
  an optical system for directing the source light to an object and directing light from the object to an imaging sensor; and
  a computational system that processes the imaging sensor data to generate phase and amplitude images of the object.

In a preferred form of the invention, there is provided a method for imaging an object with resolution less than 100 nm, the method comprising:
  providing coherent light with wavelength less than 120 nm;
  directing the light to an object and directing light from the object to an imaging sensor; and
  processing the imaging sensor data to generate phase and amplitude images of the object.

BRIEF DESCRIPTION OF THE DRAWINGS

The foregoing features of the invention will be more readily understood by reference to the following detailed description, taken with reference to the accompanying drawings wherein:
FIG. 2 is a schematic view of a digital holography setup wherein an expanding reference beam is transmitted through an object that is typically masked, and the interference pattern of the scattered beam from the object and the expanding reference beam are recorded by an imaging sensor;
FIG. 4 is a schematic view of the optics of the present invention, with a reflective object representing the EUV mask;
and
  FIG. 5 is a schematic view of the optics setup of the present invention for scanning a reflective EUV mask.

DETAILED DESCRIPTION OF THE PREFERRED EMBODIMENTS

Figure 1:
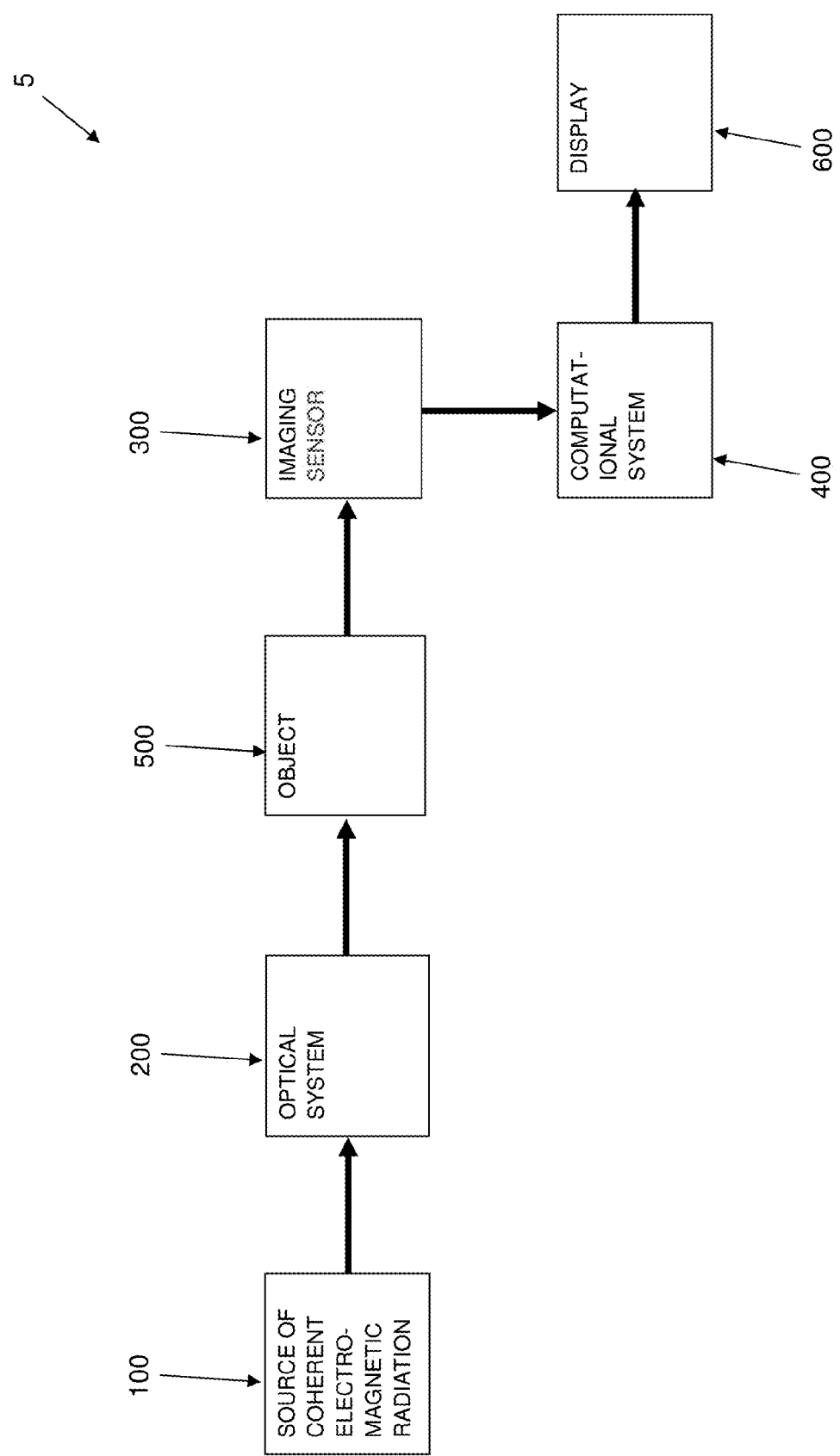
FIG. 1 is a schematic view of a novel system for providing actinic inspection of semiconductor masks.

In accordance with preferred embodiments of the present invention, and looking now at FIG. 1, there is provided a novel system 5 comprising a source of coherent electromagnetic radiation 100, typically EUV or soft x-ray, an optical system 200, an imaging sensor 300, and a computational system 400, all of which are used to produce images of an object 500 and present them on a display 600 with resolution less than 100 nm.

Source of Coherent Electromagnetic Radiation

In order to image features that are phase defects, the light source 100 must be coherent. Previously, that required using synchrotron radiation, which is produced by an accelerating beam of charged particles. More recently, researchers have found that it is possible to generate coherent beams of extreme ultraviolet (EUV, 120-10 nm) and soft x-ray (SXR, 10-0.1 nm) radiation using a process termed high harmonic generation (HHG). In this process, a pulse from an ultrafast laser, typically with a pulse length measured in femtoseconds (fs), is incident on a gas. The intense laser pulse ("the pump laser") partially ionizes the gas and excites a high harmonic of the laser frequency ("the signal beam") when the ionized electrons are accelerated and slam into the nucleus.

As it does for more conventional nonlinear optical processes such as frequency doubling, phase matching is important if a significant fraction of the light from the input laser (the pump laser) is to be converted to the new frequency or frequencies (the signal beam). One system that has been used effectively to do phase-matched HHG is a gas cell in a hollow-tube waveguide with diameter less than 1 mm. In that system, the waveguide dispersion and plasma dispersion can balance dispersion due to the neutral gas. Increased ionization due to increased laser power increases the plasma dispersion which can be compensated for by increased gas pressure, up to a critical ionization fraction that exceeds the neutral gas dispersion.

In addition to pure phase matching, significant conversion can occur with a quasi-phase matching technique. One way to implement a quasi-phase matching technique is to periodically modulate the diameter or refractive index of a hollow tube waveguide, as has been demonstrated by Ariel Paul (see Ariel J. Paul, Ph.D. Dissertation: "Coherent EUV Light from High-Order Harmonic Generation: Enhancement and Applications to Lensless Diffractive Imaging", University of Colorado, 2007). This in turn modulates the pump intensity. Given the strong non-linearity of the process, this allows conversion to occur at the peak of the beam but avoids the complementary energy flow back to the pump due to the phase mismatch.

A variety of factors—the pump wavelength, the laser pulse energy and pulse length, the noble gas chosen, the gas pressure, and the waveguide geometry—affect the efficiency of the HHG process. With optimal choices, EUV and SXR conversion efficiencies of $10^{-6}$ to $10^{-3}$ have been achieved with ultrafast lasers having average powers from 1-10 W. The resulting short wavelength beam is nearly collimated and has good beam quality and spatial coherence. These microwatt to milliwatt beams are bright enough for many imaging applications.

It is necessary to filter the longer wavelength ultrashort pulse from the high harmonics resulting from the HHG conversion. For the wavelengths of interest, this can be done by inserting one or more thin metal films (see element 105 in FIGS. 4 and 5) in the beam which are opaque to the laser wavelength but transparent to the EUV and SXR wavelengths.

It may also be necessary to filter the HHG beam so it consists of just a single harmonic. This can be done by reflecting the beam off of an EUV mirror (see element 110 in FIG. 5) whose reflective coating is frequency selective, in that the reflectivity is highest for a single harmonic wavelength and falls off rapidly away from that wavelength.

Current commercially available HHG sources are limited in the average power beam they can produce to less than 1 milliwatt. As discussed below in this specification, that may be insufficient to scan the entire mask in s a reasonable period while achieving sufficient signal-to-noise ratio (SNR). This could limit the application of systems using HHG coherent sources to tasks requiring less throughput, i.e., defect review. However, alternate sources of coherent EUV beams are available.

It is possible to generate a coherent EUV beam using a compact FEL. EUV beams with 20 mW of power have been demonstrated by Ackermann et al., at a large facility (see Operation of a free-electron laser from the extreme ultraviolet to the water window, W. Ackermann et al., Nature Photonics 1, 336-342 (2007), Published online: 1 Jun. 2007|doi:10.1038/nphoton.2007.76). A variety of approaches are being tested for developing compact devices that should yield comparable power outputs. With no driving input, an FEL will lase when spontaneous excitation begins stimulated emission in a process termed self-amplified spontaneous emission (SASE). Beams with greater temporal coherence and higher efficiency can be generated when an input beam seeds the stimulated emission. Allaria et al. demonstrated a seeded EUV FEL beam with fractional bandwidth of 0.16% ($\Delta E/E$) (see Allaria, E et al. Highly coherent and stable pulses from the FERMI seeded free-electron laser in the extreme ultraviolet (2012) In Nature Photonics 6(10). p. 699-704). Thus it appears a higher powered highly coherent EUV beam can be engineered using a compact FEL.

Optical System

These sources produce coherent EUV beams which have sufficient power, beam quality, and coherence to enable a variety of imaging modalities. For imaging amplitude and phase objects, a coherent imaging approach such as holography is preferred. However, the optics used and the various parameters of this approach must be carefully engineered to optimize the information collection. Some imaging approaches do not yield a system that simultaneously exhibits high resolution while producing real-time images.

An optimally designed system starts with the relationship between the number of pixels of the imaging sensor 300 and the number of pixels in the reconstructed image. Assuming reasonably uniform distribution (on average) of incident radiation on imaging sensor 300, one would want 2X as many pixels at the imaging sensor for an imaging method that recovers amplitude and phase. Another factor of 2 or larger is advisable to help break the symmetry of an object and its complex conjugate. Thus the target region on the object typically has, at most, ¼ the pixels of the imaging sensor.

Note that this relationship holds when the pixel scale of the imaging sensor 300 matches the scale of features of the radiation pattern incident upon it. Namely, the radiation incident on the imaging sensor should roughly cover the imaging sensor and have its significant scales resolved by the pixel scale. This requires that the object illumination should correspond to the resolvable area. If the imaging sensor is an N×N pixel array, then the resolvable area is roughly an M×M square where $M=N/2\times(k\lambda/NA)$. For a $\lambda=13.5$ nm beam with k=0.5, NA=0.125, and a 4K×4K imaging sensor, the resolvable area is roughly 110 μm square, with the resolution element 54 nm, or 13.5 nm after 4× demagnification at the wafer.

Implicit in this analysis is that the imaging sensor is sized to capture essentially all of the diffracted light and its pixels are sized accordingly so they properly sample the diffraction pattern. Analyses of the appropriate sizes and sampling for the object, wavelength, imaging sensor, and its pixel pitch that elaborate on these rules of thumb have been outlined in several publications (see Huaying Wang; Dayong Wang; Jianjun Xie; Shiquan Tao; Recording conditions of digital holography. Proc. SPIE 6279, 27th International Congress on High-Speed Photography and Photonics, 62791J (Jan. 11, 2007); doi:10.1117/12.725187; and Jorge Garcia-Sucerquia, Wenbo Xu, Stephan K. Jericho, Peter Klages, Manfred H. Jericho, and H. Jürgen Kreuzer, "Digital in-line holographic microscopy," Appl. Opt. 45, 836-850 (2006) https://doi.org/10.1364/AO.45.000836), which publications are hereby incorporated herein by reference. Their conclusions for a well designed system match these but may differ slightly based on the definition of resolution, e.g., the "k" constant in $k\lambda/NA$.

In order to match the scale of the radiation incident on the imaging sensor 300 to the size of the imaging sensor, one could set the distance from the object to the imaging sensor accordingly. However, a more compact system results when the radiation incident on the object is an expanding beam, as in FIG. 2. In general, an expanding beam can be produced by a positive (focusing) or negative optic that is either transmissive or reflective. However, to simplify the data processing, the illuminated region should be restricted to the resolvable area. For efficient use of the illuminating beam, it should just cover the resolvable area without using a masking aperture.

This last consideration drives the use of a transmissive optic to convert the coherent EUV beam to a diverging beam, due to the short focal distance for a reasonably large NA. It is easily appreciated that a reflective optic would likely interfere with the mask since it must have a focal length <1 mm given the typical beam diameter and required NA for high resolution. Although conventional transmissive optics are not available for EUV and SXR wavelengths, transmissive diffractive optics are available for EUV and SXR wavelengths.

Figure 3:
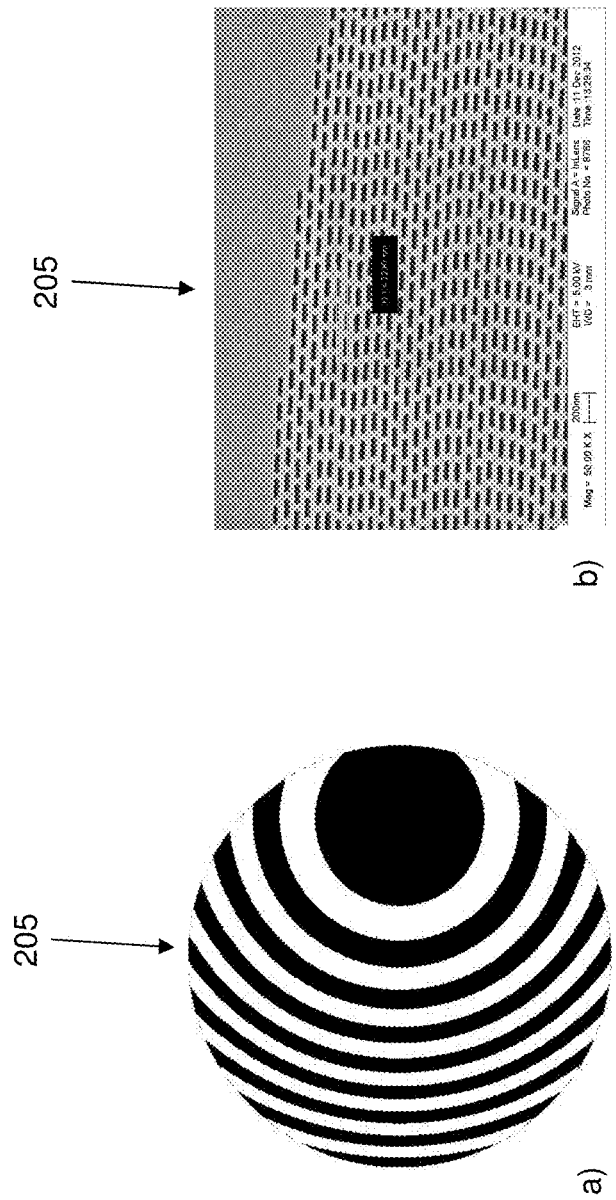
FIG. 3 is a schematic view of (a) an off-axis FZP lens and (b) a portion of a freestanding gold film FZP used in the SHARP instrument.

For these EUV and SXR wavelengths, FZP optics, a type of diffractive optic that typically has two (binary) values, can be fabricated. An FZP (see element 205 in FIGS. 3, 4 and 5) has alternating concentric rings (zones) of transmissive and opaque material as is seen in FIG. 3a. Since any substrate with sufficient mechanical stability has poor transmission at EUV and SXR wavelengths, FZPs for these wavelengths are constructed like a stencil. Typically made with a thin metal foil, the transmissive zones consist of arc-like perforations (holes) in the foil which follow the circular pattern except for some supporting ribs as is seen in FIG. 3b (see Goldberg et al., "Commissioning an EUV mask microscope for lithography generations reaching 8 nm," Proc. SPIE 8679 (2013)).

The design of the FZP is straightforward once the phase of the beam entering and exiting the FZP has been defined. The boundaries between zones are defined by locations where the optical path length of the rays connecting source and destination change by a multiple of $\lambda/2$.

For an ideal FZP, the spot size is typically quite close to the width of the outermost zone. The spot size limits the spatial coherence of the illuminating beam and hence the resolvable spot size of the reconstructed object. In order to produce as fine a pattern or spot size as possible, the metal foil FZP lens is formed by milling the foil using a focused ion beam (FIB) in order to produce the perforations. The resolution and accuracy of the FIB are critical to fabricating an FZP that shapes the beam properly. Some FIB instruments are capable of producing geometries that are accurate on scales ranging from 1-10 nm.

The FZP efficiency can be defined as the fraction of the incident radiation that is directed as intended. For a focusing lens, that would be the fraction of the beam contained within the primary or first order spot. The diffraction order is defined as the average phase step from one transmission zone to the next in waves. Thus the zero-order is the undiffracted beam. The first order is the one where the average phase difference from one zone to the next is one wave, and so on. According to diffraction theory, a certain fraction or percentage will diffract into the different orders.

For a plate that is 50% opaque, efficiency cannot be greater than 50%. Since this type of diffractive optics will diffract light into orders other than the desired one, typical diffraction efficiency into the first order is 5-30%. While that results in the loss of the majority of the coherent EUV beam, it does focus part of the collimated beam and result in a diverging beam after the focus. The object 500 (i.e., the mask or mask blank) can be positioned along the optical axis so the size of the illuminated area is close to the resolvable size of the object. Even with diffraction losses, this approach can be significantly more efficient than one that does not use optics to shape the beam. For example, it can be much more efficient than if a large, collimated beam was incident on a small object and required a masking aperture.

FZP optics offer flexibility that is difficult to achieve with more conventional optics. Namely, it is simple to add a tilt to the beam diffracted by an FZP in order to steer the beam in a particular direction. This distorts the centrosymmetric zone pattern to one that is symmetric about the projection of the tilted beam, as is shown in FIG. 3a. In addition, FZP optics enable simple fabrication of a compound lens where the original beam is divided into multiple beams, each of which can have a different focal length and beam angle. The design of multiple beam zone plates is more complex than for a single beam. However, it is straightforward to use iterative algorithms that propagate the beam(s) between the plane of the zone plate and one or more other planes, applying constraints on the amplitude or phase in each plane, to design a compound zone plate (see "Three-plane phase-only computer hologram generated with iterative Fresnel algorithm," M. Makowski; M. Sypek; A. Kolodziejczyk; G. Mikula, Opt. Eng. 44(12), 125805 (Dec. 29, 2005). doi: 10.1117/1.2148980).

Algorithm

There are a variety of means to form an image of the mask which is efficiently illuminated by a coherent EUV beam shaped by an FZP optic. For example, an imaging optic, either a FZP or reflective imaging optics, could be used to form a conventional image of the mask onto an imaging sensor. This approach is straightforward, but does not readily lend itself to easily imaging phase defects. A preferred embodiment of our invention uses digital holography to image the object.

Classical Gabor holography is shown in FIG. 2. A coherent beam, e.g. from a laser, is incident on an object. Light scattered by the object interferes with the unscattered portion of the incident (reference) beam which forms an intensity pattern in the detector plane (imaging sensor). The recorded intensity image is known as a hologram. In classical holography, the image is reconstructed by illuminating the hologram with the complex conjugate of the reference beam. In digital holography, the digitized hologram is multiplied by the complex conjugate of the reference beam and propagated back to an observation plane that typically corresponds to the position of the original object.

Mathematically, the process works as follows, where we consider the wave incident on the imaging sensor to be a sum of a reference wave, $U_R(r)$, and a scattered wave from the object, $U_O(r)$. The intensity signal measured by the imaging sensor is the square magnitude.

$$I(r)=|U_R(r)+U_O(r)|^2 \quad (1)$$

We make the usual assumption that the scattered wave is weak, relative to the reference wave. Using calibration, we subtract the unscattered portion of the reference wave resulting from $U_R(r)^2$, assume the $U_O(r)^2$ term is negligible, and divide by the average value to yield this expression for the hologram:

$$H(r) = \frac{U_R(r)^* U_O(r) + U_R(r) U_O(r)^*}{|U_R(r)|^2} \quad (2)$$

This quantity then gets propagated back to the object plane using the inverse Fresnel-Kirchoff diffraction propagation to reconstruct the object. Note that a complex (amplitude and phase) object is calculated:

$$U(R) \approx \frac{i}{\lambda} \int U_R(r) H(r) \frac{\exp(-ik|r-R|)}{|r-R|} dr \quad (3)$$

When implemented digitally, this reduces to a convolution which can be calculated by Fourier transforming the hologram, multiplying by the (precalculated) Fourier transform of the kernel, and then inverse transforming.

We note that the back propagation serves as the basis for tomographic reconstruction of the object. Changing the plane where the reconstructed object is calculated allows us to generate a 3D picture of the object. As is to be expected when the data are recorded in a plane, the resolution of the reconstruction is different in the transverse and longitudinal directions and depends on the NA of the expanding beam.

Note that the hologram mixes $U_O(r)$ and its complex conjugate due to the imaging sensor being sensitive to the intensity of the electromagnetic field. If, as pictured in FIG. 2, the reference wave is a symmetrical spherical wave, these two terms cannot be separated, which is known as the "twin problem", since the admixture of the complex conjugate adds artifacts to the reconstruction.

There are well-known ways to eliminate the twin artifact. One approach is algorithmic. One example of the algorithmic approach uses an iterative algorithm that imposes constraints to eliminate the contribution of the twin image (see Solution to the Twin Image Problem in Holography, Tatiana Latychevskaia and Hans-Werner Fink, Phys. Rev. Lett. 98, 233901(2007). Another approach makes an asymmetric measurement, either a second hologram or an off-axis reference beam, to break the symmetry of the twin images (see M. Krenkel, M. Bartels, and T. Salditt, "Transport of intensity phase reconstruction to solve the twin image problem in holographic x-ray imaging," Opt. Express 21, 2220-2235 (2013); and Emmett N. Leith and Juris Upatnieks, "Wavefront Reconstruction with Continuous-Tone Objects*," J. Opt. Soc. Am. 53, 1377-1381 (1963)). It has been demonstrated that the off-axis reference need not come from a point source but may come from an extended source, as long as it is positioned to break the symmetry of the object and its complex conjugate (see Manuel Guizar-Sicairos and James R. Fienup, "Direct image reconstruction from a Fourier intensity pattern using HERALDO," Opt. Lett. 33, 2668-2670 (2008)).

The effect of an off-axis reference point can be considered by imagining that the object and imaging sensor are at infinite conjugates. In that case, the hologram is essentially the square magnitude of the Fourier transform of the object. That is, the recorded intensity image is the square of the Fourier transform of the object. Since the reference point is in the far-field, it is nearly a plane wave which interferes with the object transform. It thus modulates the object transform with a sinusoidal fringe pattern normal to the separation vector.

Inverse transforming yields the autocorrelation of the object. The autocorrelation of an object and a point source is two copies of the object at positive and negative multiples of the separation vector plus a term at 0 separation. Another way to view this is the sinusoidal fringe pattern produces components at the positive and negative frequencies corresponding to demodulated copies of the object. Thus the object is recovered by taking the Fourier transform of the hologram and taking a region well away from 0 separation, i.e., just the object and not its complex conjugate.

With finite conjugates and Fresnel transforms, a similar approach applies. This can be seen by examining Equations 2 and 3 above and how they are numerically implemented. If the reference beam consists of an off-axis beam, then the two terms in the numerator of the right-hand side of Equation 2 can be physically separated after the propagation of those terms in Equation 3. Typical numerical implementation of the propagation equation (i.e., Equation 3) uses a split-step operator where the input field is Fourier transformed, multiplied by a phase factor, and then inverse transformed (see "Time-Dependent Propagation of High Energy Laser Beams through the Atmosphere", J. A. Fleck, Jr, J. R. Morris and M. D. Feit, UCRL-51826, UCRL-77719, and Appl. Phys. 10, 129-160 (1976)). When the propagating field is converging or diverging, the associated spherical phase is accounted for using the Talanov lens transformation as explained by Fleck et al. (see V. I. Talanov, "Focusing of light in cubic media," Soy. Phys. JETP Lett. 11, 199-201 (1970)). In any event, the isolation of the object from its complex conjugate is done by spatially segmenting the Fourier transform of the hologram before applying the phase factor and inverse transforming.

A preferred embodiment of our invention uses a compound Fresnel zone plate (CFZP) optic to form multiple beams. The simplest CFZP produces an illumination beam (beam 1) as well as a second beam (beam 2) which produces an off-axis reference point. FIG. 4 shows this approach schematically. The relative intensity, direction, and NA of each beam is set by the design of the CFZP. The relative intensity of each beam can be adjusted by controlling the fraction of the incident coherent EUV beam that is directed into each particular beam. The direction of the beam is set by the symmetry of the FZP, i.e., whether the zone pattern corresponding to that beam is centered or offset. The NA of each beam is set by the primary focus of the beam relative to its diameter at the zone plate.

The beams formed by the CFZP are spatially and temporally coherent. Thus, at the detection plane at the image sensor, they interfere. Ideally, reference beam 2 has a perfectly spherical wavefront whose origin is offset from that of beam 1. The interference ideally imposes a sinusoidal fringe pattern on beam 1 which is diffracted by the mask/object. In order to reconstruct the phase of beam 1 with maximal SNR, the beams should be completely coherent. In practice, limited spatial or temporal coherence reduces the visibility of the interference pattern. Ideally, the temporal coherence is such that the fractional bandwidth of the coherent beam, $\lambda/\Delta\lambda$, exceeds the number of linear pixels across the reconstructed image, in order to have high visibility of the interference pattern. If the temporal coherence is shorter and the corresponding fractional bandwidth is smaller, the SNR of the reconstructed image is reduced compared to a beam with full coherence.

Note that for an off-axis reference point whose small focal spot is in the plane of an arbitrary mask, it is not certain that the center of the focal spot will be on a reflective or non-reflective region of the mask, thereby introducing uncertainty as to the intensity of the reference beam. Therefore, it is preferable to have the reference beam focus some distance off of the mask surface. The size of the out-of-focus spot hitting the mask can be designed to ensure that a predictable fraction of the spot will be on a reflective region of the mask. This ensures that the reference beam will have the appropriate intensity to form an interference pattern with sufficient contrast at the imaging sensor. The known focal position of the reference beam is used when performing the digital back propagation to reconstruct the mask reflectance.

We expect that the particular portion of the mask which reflects the beam corresponding to the off-axis point will have some influence on the beam and hence on the diffraction pattern. Thus, it may introduce some distortion to the recovered image illuminated by beam 1. With complete knowledge of the design of the mask and the CFZP, it is possible to calculate that distortion and remove it, thereby recovering an undistorted region illuminated by beam 1.

However, that introduces some complication to the algorithms and computations required. It may be simpler to add 2 small planar mirrors to the assembly holding the CFZP.

These mirrors direct beam 2 so it interferes with the reflection of beam 1 by the mask, but without distorting it with a non-uniform reflection by the mask. Two mirrors are required so that the path length to the imaging sensor for both beam 1 and 2 are equal in order to maximize the visibility of the interference of the beams.

It is important to analyze where the light diffracted by the zone plate into orders other than the first order will end up. It may be necessary to insert one or more stops or apertures to prevent light from these unwanted orders contributing to the hologram.

It is also important to use appropriate computational methods to digitally propagate the hologram as if illuminated by the complex conjugate of the reference beam. Our explanation of the utility of an off-axis reference beam assumed that the object and imaging sensor were at infinite conjugates, i.e., the imaging sensor was in the far field of the object. In general, that condition will not apply when diverging beams are used to match the size of the hologram to the imaging sensor and a finite conjugate implementation of the diffraction integral in Equation 3 must be used.

Another consideration is that it is desirable to image a relatively large two-dimensional surface, although as we have seen, only an area some tens of microns across can be imaged in a single exposure. It is straightforward to translate the object so images from multiple exposures overlap so that the entire surface is imaged at high resolution. However, the optical system must be modified so the translation of the object does not interfere with any of the beams or with the imaging sensor. For example, the 45 degree reflection shown in FIG. 4 would limit the distance the object could be translated, in the plane of the object's surface, before it might interfere with the plane of the imaging sensor.

For such a scanning imaging system, a preferred embodiment has the illumination beam initially parallel to the two-dimensional surface, as shown in FIG. 5. A small, relatively inexpensive flat mirror can then be used to direct the beam so it is nearly normal to the surface. The compound zone plate optic then forms the same two beams as shown in FIG. 4, except that they are nearly normal to the surface. The optic must also include a clear aperture so the reflected beams pass through without being obstructed. With this approach, the object being imaged at high resolution can be arbitrarily translated along its two-dimensional surface without interfering with the beams or the imaging sensor.

The EUV mask size and required resolution impose requirements on the throughput of a system which can scan an entire mask. Consider an EUV mask with 132 mm×104 mm useful area and a system which images a 110 micron square with each exposure. This system requires 8.58 million exposures to cover the mask. If an inspection takes 12 hours, this requires 1 image every 0.038 s, a 26 Hz image rate. If half that time is spent performing the exposure and half the time moving the mask relative to the optics, each s move happens in 0.019 s.

Assuming the motion profile is constant (maximum) acceleration for ½ of the move followed by constant (maximum) deceleration, the mask must accelerate at 1.21 m/s$^2$, or 0.12 G where G is the acceleration of gravity. The maximum speed attained at the midway point is 11.6 mm/s. This can be achieved by existing stages such as the Newport DynamYX® DATUM® Ultra-High Performance Air Bearing Stage which has 25 nm repeatability, 200 nm accuracy, accelerates at 3 G in one horizontal direction and 5 G in the other, and has a maximum speed of 1000 mm/s.

The 26 Hz image rate requires a high pixel digitization rate. The pixel readout takes place while the mask is in motion, i.e., in 0.019 s. Thus the 4K×4K sensor requires a pixel readout rate of 0.84 Gpix/s. Both the array size and readout rate are well within industry capabilities as exemplified by 4K HDTV imaging sensors, e.g., the Sony sensor in the HDC-4800 camera with ~8 Mpixels at 480 frames per second (fps).

We can estimate the beam energy per exposure as follows. A typical well depth for a pixel is 200,000 electrons. Consider that the average illumination is 50% of the well depth and that each EUV photon, with energy 91.84 eV, produces 27 electrons when detected. Thus each pixel detects 3703 EUV photons per pixel, on average. Assuming a 4K×4K array and a 10% efficiency of the zone plate, each exposure requires 5.71E13 eV or 9.14E-6 Joules. With the 26 Hz image rate and a 50% duty cycle for useful illumination, while the mask is stationary, this requires 0.48 mW of coherent EUV power. This power level appears difficult to achieve using HHG at 13.5 nm. However, it is well within the capability of FEL systems.

Note that for an optimally designed system, the exposure rate and required beam power go as the inverse square of the resolution length if the total inspection time remains constant (12 hours). Halving the resolution length halves the resolvable field width and quadruples the number of exposures, the exposure rate, and the required power level. The required acceleration of the stage holding the mask increases by $2^4=16$.

These estimates of the required beam power, acceleration, and image rate give the rough parameters of a system that could perform comprehensive mask inspection. The design of an optimal system will adjust the system parameters according to the specifications of the components. For example, it could be advantageous to change the times alloted to stage motion and exposure. The exemplary system described has a 50% duty cycle. However, the stage referenced has acceleration and speed that far exceed the requirements, enabling it to perform the move more quickly and increase the fraction of time for each exposure.

For a system designed for large transmission objects, the same principle applies in that the illumination beam is initially parallel to the object surface before reflection by a plane mirror at 45 degrees to the beam axis.

MODIFICATIONS

The described embodiments of the invention are intended to be merely exemplary and numerous variations and modifications will be apparent to those skilled in the art. All such variations and modifications are intended to be within the scope of the present invention.

Among other things, it will be appreciated by those skilled in the art that the invention described herein is not limited in application to semiconductor masks or mask blanks but may be applied to imaging a variety of objects. It will also be appreciated by those skilled in the art that the invention is not limited to quasi-planar objects, but may be applied to objects where the source light interacts over some significant depth of the object, especially when holographic imaging techniques that can reconstruct the object as a function of depth are employed. These and other variations are considered to be within the scope of the present invention.

What is claimed is:

1. An apparatus for imaging an object with resolution less than 100 nm, the apparatus comprising:
   a coherent light source with wavelength less than 120 nm;
   an optical system for directing the source light to an object and directing light from the object to an imaging sensor, where the optical system comprises a compound zone plate optic comprising a transmissive diffractive optic which divides the source light into a first beam and a second, different beam and directs the first beam to illuminate the object and directs the second beam to interfere with the first beam; and a computational system that processes the imaging sensor data to generate phase and amplitude images of the object.

2. An apparatus according to claim 1 where the coherent light source uses high harmonic generation (HHG) for producing the source light.

3. An apparatus according to claim 1 where the coherent light source uses a free electron laser (FEL) for producing the source light.

4. An apparatus according to claim 1 where the optical system comprises a zone plate optic to illuminate the object with a diverging beam.

5. An apparatus according to claim 1 where the optical system comprises a series of mirrors to direct the second beam.

6. An apparatus according to claim 1 where the second beam illuminates a portion of the object.

7. An apparatus according to claim 1 which uses the identical (actinic) wavelength as a semiconductor lithography apparatus wherein the object is a mask designed for semiconductor lithography.

8. A method for imaging an object with resolution less than 100 nm, the method comprising:

providing coherent light with wavelength less than 120 nm;

directing the light to an object and directing light from the object to an imaging sensor, wherein a compound zone plate optic comprising a transmissive diffractive optic is used to divide the light into a first beam and a second, different beam and direct the first beam to illuminate the object and direct the second beam to interfere with the first beam; and processing the imaging sensor data to generate phase and amplitude images of the object.

9. A method according to claim 8 where the coherent light is produced using high harmonic generation (HHG).

10. A method according to claim 8 where the coherent light is produced using a free electron laser (FEL).

11. A method according to claim 8 wherein a zone plate optic is used to illuminate the object with a diverging beam.

12. A method according to claim 8 wherein a series of mirrors are used to direct the second beam.

13. A method according to claim 8 wherein the second beam illuminates a portion of the object.

14. A method according to claim 8 which uses the identical (actinic) wavelength as a semiconductor lithography apparatus wherein the object is a mask designed for semiconductor lithography.

\* \* \* \* \*